US008609146B2

(12) United States Patent
Sill et al.

(10) Patent No.: US 8,609,146 B2
(45) Date of Patent: Dec. 17, 2013

(54) MULTI-BLOCK COPOLYMERS FOR THE PREPARATION OF STABILIZED MICELLES

(71) Applicant: Intezyne, Inc., Tampa, FL (US)

(72) Inventors: Kevin Sill, Tampa, FL (US); Habib Skaff, Tampa, FL (US)

(73) Assignee: Intezyne Technologies, Inc., Tampa, FL (US)

( * ) Notice: Subject to any disclaimer, the term of this patent is extended or adjusted under 35 U.S.C. 154(b) by 0 days.

(21) Appl. No.: 13/621,652

(22) Filed: Sep. 17, 2012

(65) Prior Publication Data

US 2013/0078310 A1   Mar. 28, 2013

Related U.S. Application Data

(60) Provisional application No. 61/536,297, filed on Sep. 19, 2011.

(51) Int. Cl.
| | | |
|---|---|---|
| *A61K 9/14* | (2006.01) | |
| *A61K 47/34* | (2006.01) | |
| *A61K 47/32* | (2006.01) | |
| *C01G 49/02* | (2006.01) | |
| *C01G 9/02* | (2006.01) | |
| *A61K 9/107* | (2006.01) | |
| *C08G 18/62* | (2006.01) | |

(52) U.S. Cl.
CPC ............... *A61K 9/1075* (2013.01); *A61K 9/14* (2013.01); *A61K 47/32* (2013.01); *A61K 47/34* (2013.01); *C01G 49/02* (2013.01); *C01G 9/02* (2013.01); *C08G 18/6225* (2013.01); *Y10S 977/906* (2013.01)
USPC .................... 424/489; 423/594.1; 423/594.14; 423/622; 423/632; 528/361; 977/906

(58) Field of Classification Search
None
See application file for complete search history.

(56) References Cited

U.S. PATENT DOCUMENTS

| | | | |
|---|---|---|---|
| 2004/0228823 A1* | 11/2004 | Bronich et al. ............ | 424/70.16 |
| 2006/0172914 A1 | 8/2006 | Breitenkamp et al. | |
| 2006/0240092 A1 | 10/2006 | Breitenkamp et al. | |
| 2008/0274173 A1 | 11/2008 | Sill et al. | |

OTHER PUBLICATIONS

BP Bastakoti, S Guragain, Y Yokoyama, SI Yusa, K Nakashima. "Synthesis of Hollow CaCO3 Nanospheres Templated by Micelles of Poly(styrene-b-acrylic acid-b-ethylene glycol) in Aqueous Solutions." Langmuir, vol. 27(1), 2011, pp. 379-384, Published on Web Nov. 30, 2010.*
Ma, J., et al., Well-Defined Polymers Bearing Pendent Alkene Functionalities via Selective RAFT Polymerization, Received Sep. 9, 2008; Revised Manuscript Received Oct. 13, 2008, Macromolecules is published by the American Chemical Society, 1-11 pp.

Joralemon, M. J., et al., Synthesis, Characterization, and Bioavailability of Mannosylated Shell Cross-Linked Nanoparticles, © 2004 American Chemical Society, Biomacromolecules, vol. 5, No. 3, 2004, 903-913 pp.
Wooley, K. L, et al., pH-Responsive Shell Cross-Linked Nanoparticles with Hydrolytically Labile Cross-Links, American Chemical Society, A-C, Aug. 19, 2008.
Wooley, K. L., et al., Folic acid-conjugated nanostructured materials designed for cancer cell targeting, This journal is © The Royal Society of Chemistry 2003, 2400-2401 pp.
Zhang, K., et al., Cationic shell-crosslinked knedel-like nanoparticles for highly efficient gene and oligonucleotide transfection of mammalian cells, Biomaterials (2009), doi:10.1016/j.biomaterials.2008. 10.057, 1-10 pp.
Walker, G. F., et al., Toward Synthetic Viruses: Endosomal pH-Triggered Deshielding of Targeted Polyplexes Greatly Enhances Gene Transfer in Vitro and in Vivo, Molecular Therapy, vol. 11, No. 3, Mar. 2005, Copyright The American Society of Gene Therapy, 418-425 pp.
McCormick, C. L., et al., Synthesis of Reversible Shell Cross-Linked Micelles for Controlled Release of Bioactive Agents, Copyright American Chemical Society, A-C, Mar. 21, 2006.
Stenzel, M. H., et al., RAFT polymerization: an avenue to functional polymeric micelles for drug delivery, This journal is copyright The Royal Society of Chemistry 2008, Chem. Commun., 2008, 3486-3503 pp.
El-Sayed, M. E. H., et al., Rational design of composition and activity correlations for pH-responsive and glutathione-reactive polymer therapeutics, copyright 2005 Elsevier B.V., Journal of Controlled Release 104 (2005) 417-427 pp.
Rios-Doria, J., et al., A Versatile PolymerMicelle Drug Delivery System for Encapsulation and In Vivo Stabilization of Hydrophobic Anticancer Drugs, Hindawi Publishing Corporation, Journal of Drug Delivery, vol. 2012, Article ID 951741, 1-8 pp.
Rapoport, N., Physical stimuli-responsive polymeric micelles for anti-cancer drug delivery, Prog. Polym. Sci. 32 (2007) 962-990 pp.
Nostrum, C. F. Van, et al., Triggered destabilisation of polymeric micelles and vesicles by changing polymers polarity: An attractive tool for drug delivery, Journal of Controlled Release 120 (2007) 131-148 pp.
McCormick, C. L., et al., Aqueous RAFT Synthesis of Micelle-Forming Amphiphilic Block Copolymers Containing N-Acryloylvaline. Dual Mode, Temperature/pH Responsiveness, and "Locking" of Micelle Structure through Interpolyelectrolyte Complexation, © 2007 American Chemical Society, Macromolecules, vol. 40, No. 18, 2007, 6473-6480 pp.
McCormick, C. L., et al., Advances in the synthesis of amphiphilic block copolymers via RAFT polymerization: Stimuli-responsive drug and gene delivery, A.W. York et al. / Advanced Drug Delivery Reviews 60 (2008) 1018-1036 pp.

(Continued)

*Primary Examiner* — Frederick Krass
*Assistant Examiner* — Isaac Shomer
(74) *Attorney, Agent, or Firm* — Kevin N. Sill

(57) ABSTRACT

The present invention relates to the field of polymer chemistry and more particularly to multiblock copolymers and micelles comprising the same. Compositions herein are useful for drug-delivery applications.

1 Claim, No Drawings

(56) References Cited

OTHER PUBLICATIONS

McCormick, C. L., et al., RAFT Synthesis of a Thermally Responsive ABC Triblock Copolymer Incorporating N-Acryloxysuccinimide for Facile in Situ Formation of Shell Cross-Linked Micelles in Aqueous Media, © American Chemical Society, A-I, 2006.

McCormick, C. L., et al., Synthesis of Reversible Shell Cross-Linked Micelles for Controlled Release of Bioactive Agents, © 2006 American Chemical Society, Macromolecules, vol. 39, No. 8, 2006, 39, 2726-2728 pp.

* cited by examiner

MULTI-BLOCK COPOLYMERS FOR THE PREPARATION OF STABILIZED MICELLES

CROSS REFERENCE TO RELATED APPLICATIONS

The present application claims priority to U.S. provisional patent application Ser. No. 61/536,297, filed Sep. 19, 2011, the entirety of which is hereby incorporated by reference herein.

FIELD OF THE INVENTION

The present invention relates to the field of polymer chemistry and more particularly to block copolymers, uses thereof, and intermediates thereto.

BACKGROUND OF THE INVENTION

The development of new therapeutic agents has dramatically improved the quality of life and survival rate of patients suffering from a variety of disorders. However, drug delivery innovations are needed to improve the success rate of these treatments. Specifically, delivery systems are still needed which effectively minimize premature excretion and/or metabolism of therapeutic agents and deliver these agents specifically to diseased cells thereby reducing their toxicity to healthy cells.

Rationally-designed, nanoscopic drug carriers, or "nanovectors," offer a promising approach to achieving these goals due to their inherent ability to overcome many biological barriers. Moreover, their multi-functionality permits the incorporation of cell-targeting groups, diagnostic agents, and a multitude of drugs in a single delivery system. Polymer micelles, formed by the molecular assembly of functional, amphiphilic block copolymers, represent one notable type of multifunctional nanovector.

Polymer micelles are particularly attractive due to their ability to deliver large payloads of a variety of drugs (e.g. small molecule, proteins, and DNA/RNA therapeutics), their improved in vivo stability as compared to other colloidal carriers (e.g. liposomes), and their nanoscopic size which allows for passive accumulation in diseased tissues, such as solid tumors, by the enhanced permeation and retention (EPR) effect. Using appropriate surface functionality, polymer micelles are further decorated with cell-targeting groups and permeation enhancers that can actively target diseased cells and aid in cellular entry, resulting in improved cell-specific delivery.

While self assembly represents a convenient method for the bottom-up design of nanovectors, the forces that drive and sustain the assembly of polymer micelles are concentration dependent and inherently reversible. In clinical applications, where polymer micelles are rapidly diluted following administration, this reversibility, along with high concentrations of micelle-destabilizing blood components (e.g. proteins, lipids, and phospholipids), often leads to premature dissociation of the drug-loaded micelle before active or passive targeting is effectively achieved. For polymer micelles to fully reach their cell-targeting potential and exploit their envisioned multi-functionality, in vivo circulation time must be improved. Drug delivery vehicles are needed, which are infinitely stable to post-administration dilution, can avoid biological barriers (e.g. reticuloendothelial system (RES) uptake), and deliver drugs in response to the physiological environment encountered in diseased tissues, such as solid tumors.

DETAILED DESCRIPTION OF CERTAIN EMBODIMENTS OF THE INVENTION

I. General Description

According to one embodiment, the present invention provides a micelle comprising a multiblock copolymer which comprises a polymeric hydrophilic block, optionally a crosslinkable or crosslinked polymeric block, and a polymeric hydrophobic block, characterized in that said micelle has an inner core, optionally a crosslinkable or crosslinked outer core, and a hydrophilic shell. It will be appreciated that the polymeric hydrophilic block corresponds to the hydrophilic shell, the optionally crosslinkable or crosslinked polymeric block corresponds to the optionally crosslinked outer core, and the polymeric hydrophobic block corresponds to the inner core.

In certain embodiments, the present invention provides a micelle having an drug encapsulated therein, wherein said micelle comprises a multiblock copolymer which comprises:
  a polymeric hydrophilic block;
  a crosslinked outer core block; and
  a polymeric hydrophobic block.

The hydrophobic forces that drive the aqueous assembly of colloidal drug carriers, such as polymer micelles and liposomes, are relatively weak, and these assembled structures dissociate below a finite concentration known as the critical micelle concentration (CMC). The CMC value of polymer micelles is of great importance in clinical applications because drug-loaded colloidal carriers are diluted in the bloodstream following administration and rapidly reach concentrations below the CMC (μM or less). This dilution effect will lead to micelle dissociation and drug release outside the targeted area and any benefits associated with the micelle size (EPR effect) or active targeting will be lost. While a great deal of research throughout the 1990's focused on identifying polymer micelles with ultra-low CMC values (nM or less), Maysinger (Savic et. al., *Langmuir,* 2006, p3570-3578) and Schiochet (Lu et. al., *Macromolecules,* 2011, p6002-6008) have redefined the concept of a biologically relevant CMC by showing that the CMC values for polymer micelles shift by two orders of magnitude when the CMC values in saline are compared with and without serum.

Despite the large volume of work on micellar drug carriers, little effort has focused on improving their in vivo stability to dilution. One potential reason is that the true effects of micelle dilution in vivo are not fully realized until larger animal studies are utilized. Because a mouse's metabolism is much higher than larger animals, they can receive considerably higher doses of toxic drugs when compared to larger animals such as rats or dogs. Therefore, when drug loaded micelles are administered and completely diluted throughout the entire blood volume, the corresponding polymer concentration will always be highest in the mouse model. Therefore, it would be highly desirable to prepare a micelle that is stabilized (crosslinked) to dilution within biological media.

In some embodiments, compounds of the present invention are capable of polymerizing additional unsaturated monomers by controlled free radical polymerization ("CFRP"), or "living" radical polymerization. One of ordinary skill in the art would recognize that CFRP can be used to polymerize unsaturated monomers in a fashion whereby chain transfer and termination reactions can be minimized resulting in the growth of one or more polymer blocks with predictable polymer length and polydispersity index (PDI). Vinyl monomers capable of undergoing CFRP include styrene, methyl methacrylate, acrylic acid, to name but a few.

In some embodiments, compounds of the present invention possess a stable, nitroxide free radical moiety (—O—N(R°)$_2$.) capable of nitroxide mediated radical polymerization (NMRP). In other embodiments, compounds of the present invention perform reversible addition-fragmentation chain transfer polymerization (RAFT). RAFT agents typically possess dithioester or trithiocarbonate functionality, among others, and can polymerize a wide range of monomers including, but not limited to, styrene and acrylate derivatives. In still other embodiments, compounds of the present invention possess functionality capable of performing atom transfer radical polymerization (ATRP). These functionalities include those that are halogenated (e.g. bromine) and form stable free radicals capable of polymerizing a wide range of unsaturated compounds. In certain cases, additional catalytic reagents (e.g. transition metal catalysts and appropriate organic ligands) are optionally added to improve the kinetics of ATRP.

Without wishing to be bound by any particular theory, it is believed that in each of these controlled radical polymerizations, the radical chain end is trapped in a dormant state for a large majority of the polymerization. However, equilibrium exists between this dormant state and an active radical chain end that is capable of polymerizing vinyl monomers. Thus a dynamic equilibrium exists that allows for the capping group to disassociate from the chain end, radically add one or more monomer units, then return to the protected state. The relevance of the protected state is that the number of active radicals in the polymerization at any given time is greatly reduced and termination events are nearly eliminated, giving rise to narrow (<1.2) polydispersity indices and predictable molecular weights. Each polymerization technique has it's own respective strengths and shortcomings, and each offer varying degree of control over molecular weight and polydispersity. NMRP offers a very simple approach whereby typically no additional radical initiators or metals are used. However, the controlled polymerization of acrylate monomers is difficult. RAFT employs a dithioester or trithiocarbonate functionality as the chain transfer group following initiation with a radical source for the polymerization of a wide range of monomers including, but not limited to, styrene and acrylate derivatives. ATRP utilizes a halogen atom, typically bromine, as the radical capping group. A copper catalyst and amine ligands are used to disassociate the bromine from the secondary, tertiary, or benzyl carbon to generate the radical. ATRP also polymerizes a wide range of vinyl monomers and operates at lower temperatures (room temperature) than nitroxide or RAFT polymerizations.

2. Definitions

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

One skilled in the art will recognize that a monomer repeat unit is defined by parentheses around the repeating monomer unit. The number (or letter representing a numerical range) on the lower right of the parentheses represents the number of monomer units that are present in the polymer chain. In the case where only one monomer represents the block (e.g. a homopolymer), the block will be denoted solely by the parentheses. In the case of a mixed block, multiple monomers comprise a single, continuous block. It will be understood that brackets will define a portion or block. For example, one block may consist of four individual monomers, each defined by their own individual set of parentheses and number of repeat units present. All four sets of parentheses will be enclosed by a set of brackets, denoting that all four of these monomers combine in random, or near random, order to comprise the mixed block. For clarity, the randomly mixed block of [BCADDCBADABCDABC] would be represented in shorthand by [(A)$_4$(B)$_4$(C)$_4$(D)$_4$].

As used herein, the term "polymeric hydrophilic block" refers to a polymer that is not a poly(amino acid) and is hydrophilic in nature. Such hydrophilic polymers are well known in the art and include polyethylene oxide (also referred to as polyethylene glycol or PEG), and derivatives thereof, poly(N-vinyl-2-pyrolidone), and derivatives thereof, poly(N-isopropylacrylamide), and derivatives thereof, poly(hydroxyethyl acrylate), and derivatives thereof, poly(hydroxyethyl methacrylate), and derivatives thereof, and polymers of N-(2-hydroxypropoyl)methacrylamide (HMPA) and derivatives thereof, quaternized poly(vinyl pyridine) and derivatives thereof.

As used herein, the term "polymeric hydrophobic block" refers to a polymer that is not a poly(amino acid) and is hydrophobic in nature. Such hydrophobic polymers are well known in the art and include polystyrene (PS) and derivatives thereof, poly(methyl methacrylate) (PMMA), polymethacrylate (PMA), poly(butyl acrylate), poly(lauryl acrylate) and derivatives thereof.

As used herein, the term "optionally crosslinkable polymeric block" refers to a carboxylic acid containing polymeric block that is not a poly(amino acid). Such polymers are well known in the art and include, but are not limited to, poly(acrylic acid) and poly(methacrylic acid).

As used herein, the term "crosslinked polymeric block" refers to a carboxylic acid containing polymeric block that is chemically crosslinked to another carboxylic acid containing block on a separate polymer chain. One such method of accomplishing the chemical crosslinking is with the use of metal ions, which is described in more detail herein, infra.

As used herein, the phrase "living polymer chain-end" refers to the terminus resulting from a polymerization reaction that maintains the ability to react further with additional monomer or with a polymerization terminator.

As used herein, the term "termination" refers to attaching a terminal group to a polymer chain-end by the reaction of a living polymer with an appropriate compound. Alternatively, the term "termination" may refer to attaching a terminal group to an amine or hydroxyl end, or derivative thereof, of the polymer chain.

As used herein, the term "polymerization terminator" is used interchangeably with the term "polymerization terminating agent" and refers to a compound that reacts with a living polymer chain-end to afford a polymer with a terminal group. Alternatively, the term "polymerization terminator" may refer to a compound that reacts with an amine or hydroxyl end, or derivative thereof, of the polymer chain, to afford a polymer with a terminal group.

As used herein, the term "polymerization initiator" refers to a compound, which reacts with, or whose anion or free base form reacts with, the desired monomer in a manner that results in polymerization of that monomer. In certain embodiments, the polymerization initiator is the compound that reacts with an alkylene oxide to afford a polyalkylene oxide block. In other embodiments, the polymerization initiator is an amine salt as described herein. In certain embodiments, the polymerization initiator is a trifluoroacetic acid amine salt.

As used herein, the term "nitroxide" refers to a compound that represents a stable amine oxide free radical that is useful for mediating radical polymerizations. Specific examples of nitroxides are 2,2,6,6-Tetramethylpiperidine-1-oxyl (TEMPO), 4-hydroxy-TEMPO (TEMPOL), and 4-acetamido-TEMPO.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N($R^\dagger$)— as in N-substituted pyrrolidinyl.

The term "unsaturated", as used herein, means that a moiety has one or more units of unsaturation.

As used herein, the term "bivalent, saturated or unsaturated, straight or branched $C_{1-12}$ hydrocarbon chain", refers to bivalent alkylene, alkenylene, and alkynylene chains that are straight or branched as defined herein.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$NO_2$; —CN; —$N_3$; —$(CH_2)_{0-4}N(R^\circ)_2$; —)$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR—$, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R$; —$C(O)C(O)R^\circ$; —$C(O)CH_2C(O)R$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene) O—$N(R^\circ)_2$; or —$(C_{1-4}$ straight or branched)alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2^\bullet$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4})$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O—$, or —$S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. A suitable tetravalent substituent that is bound to vicinal substitutable methylene carbons of an "optionally substituted" group is the dicobalt hexacarbonyl cluster represented by

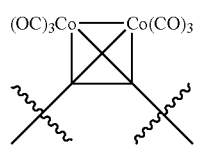

when depicted with the methylenes which bear it.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, —(haloR●), —OH, —OR●, —O(haloR●), —CN, —C(O)OH, —C(O)OR●, —NH$_2$, —NHR●, —NR●$_2$, or —NO$_2$, wherein each R. is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted C$_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as in neutron scattering experiments, as analytical tools or probes in biological assays.

3. Description of Exemplary Embodiments

A. Triblock Copolymers

In certain embodiments, the present invention provides a multiblock copolymer of formula I:

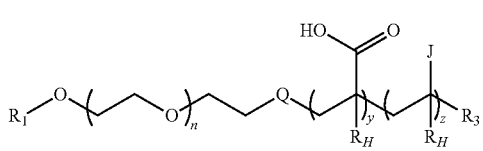

I wherein:
n is 40-500;
y is 5-50;
z is 10-200;
each Q group is independently selected from a valence bond or a bivalent, saturated or unsaturated, straight or branched $C_{1-20}$ alkylene chain, wherein 0-9 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
each J group is independently selected from a saturated or unsaturated, straight or branched $C_{1-20}$ alkylene chain, wherein 0-9 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^H$ is hydrogen, —CH$_3$, or —CH$_2$—CH$_3$;
$R^1$ is hydrogen, —N$_3$, —CN, a suitable amine protecting group, a protected aldehyde, a protected hydroxyl, a suitable hydroxyl protecting group, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur;
$R^3$ is a selected from hydrogen, a halogen, an optionally substituted aliphatic group

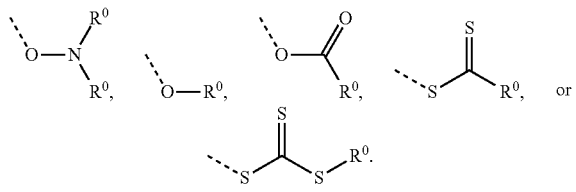

As defined generally above, n is 40-500. In certain embodiments, n is about 225. In some embodiments, n is about 275. In other embodiments, n is about 110. In other embodiments, n is about 40 to about 60. In other embodiments, n is about 60 to about 90. In still other embodiments, n is about 90 to about 150. In other embodiments, n is about 150 to about 200. In some embodiments, n is about 200 to about 300, about 300 to about 400, about 400 to about 500. In still other embodiments, n is about 250 to about 280. In other embodiments, n is about 300 to about 375. In other embodiments, n is about 400 to about 500. In certain embodiments, n is selected from 50±10. In other embodiments, n is selected from 80±10, 115±10, 180±10, 225±10, 275±10, or 450±10.

In certain embodiments, y is 5-50. In other embodiments, y is 5-25. In other embodiments, y is 5-10. In other embodiments, y is 10-20. In other embodiments, y is selected from 5±3, 10±5, 15±5, 20±5, 30±10, or 40±10.

In certain embodiments, the z group is about 10 to about 200. In certain embodiments, the z group is about 25. In other embodiments, z is about 10 to about 50. In other embodiments, z is about 50. According to yet another embodiment, z is about 75. In other embodiments, z is about 100. In certain embodiments, z is about 40 to about 80. In other embodiments, z is selected from 10±5, 15±5, 25±5, 50±5, 75±10, 100±10, or 125±10.

According to another embodiment, the present invention provides compounds of formula I, as described above, wherein said compounds have a polydispersity index ("PDI") of about 1.0 to about 1.2. According to another embodiment, the present invention provides compounds of formula I, as described above, wherein said compound has a polydispersity index ("PDI") of about 1.03 to about 1.15. According to yet another embodiment, the present invention provides compounds of formula I, as described above, wherein said compound has a polydispersity index ("PDI") of about 1.10 to about 1.20. According to other embodiments, the present invention provides compounds of formula I having a PDI of less than 1.50.

As generally described above, $R^3$ is a selected from hydrogen, a halogen, an optionally substituted aliphatic group,

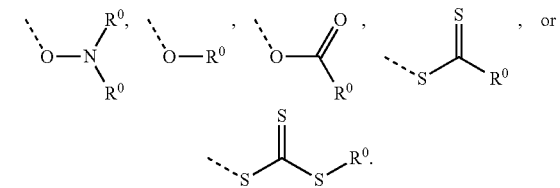

Specific examples of R³ groups can be found in Table 1.

TABLE 1

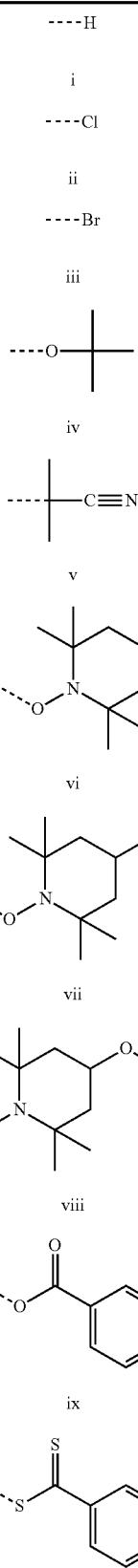

TABLE 1-continued

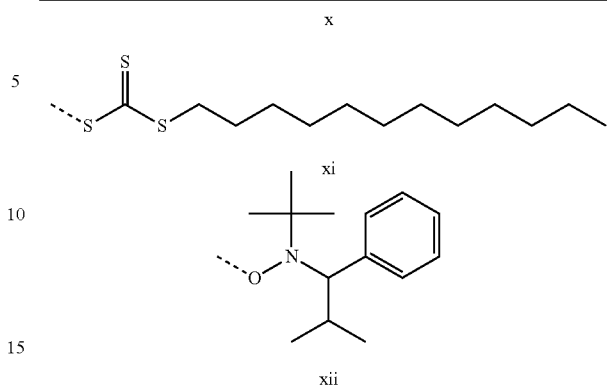

In certain embodiments, the J group represents a side chain group of a hydrophobic polymer block. In certain embodiments, the J group represents a side chain of polystyrene. In other embodiments, the J group represents a side chain of poly(methyl acrylate). In yet other embodiments, the J group represents a side chain of poly(methacrylate).

Specific examples of J groups can be found in Table 2.

TABLE 2

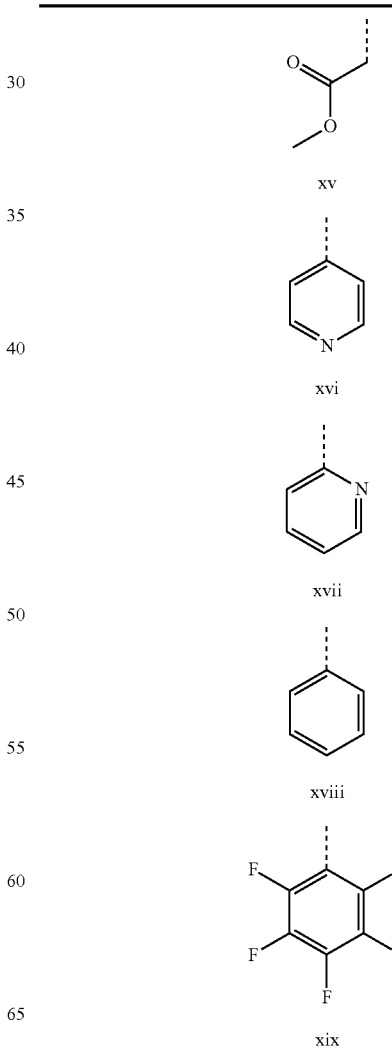

TABLE 2-continued

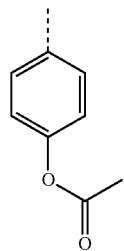

xx

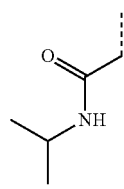

xxi

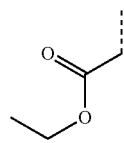

xxii

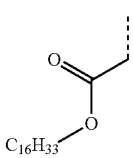

xxiii

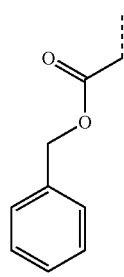

xxiv

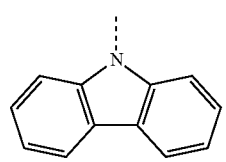

xxv

|
Cl xxvi

TABLE 2-continued

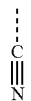

xxvii

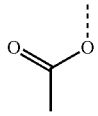

xxviii

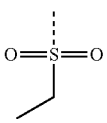

xxix

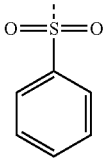

xxx

In certain embodiments, the present invention provides a multiblock copolymer of formula II:

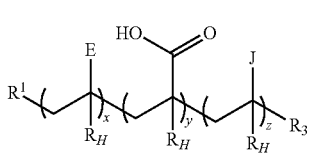

II wherein each of $R^1$, J, $R_H$, y, z, and $R^3$ is as defined above and as described in classes and subclasses herein, both singly and in combination;

x is 10-200;

each E group is independently selected from a saturated or unsaturated, straight or branched $C_{1-20}$ alkylene chain, wherein 0-9 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, the x group is about 10 to about 200. In certain embodiments, the x group is about 25. In other embodiments, x is about 10 to about 50. In other embodiments, x is about 50. According to yet another embodiment, x is about 75. In other embodiments, x is about 100. In certain embodiments, x is about 40 to about 80. In other embodiments, x is selected from 10±5, 15±5, 25±5, 50±5, 75±10, 100±10, or 125±10.

In certain embodiments, the E group represents a side chain group of a hydrophilic polymer block. In certain embodiments, the E group represents a side chain of poly(N-vinyl-2-pyrolidone). In other embodiments, the E group represents a side chain of poly(vinyl alcohol). In yet other embodiments, the E group represents a side chain of poly(hydroxyethyl acrylate).

Specific examples of E groups can be found in Table 3.

TABLE 3

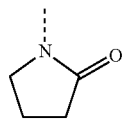

xl

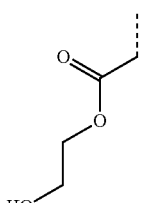

xli

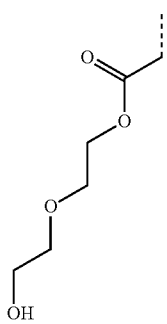

xlii

xliii

In certain embodiments, the present invention provides a multiblock copolymer of formula III:

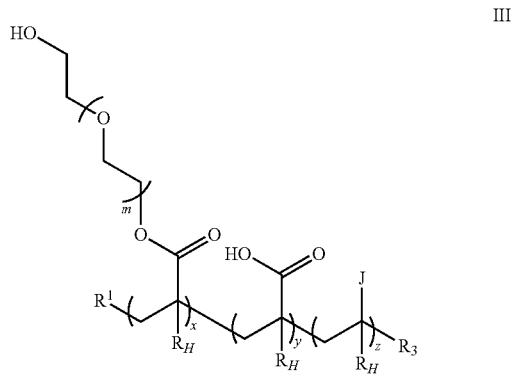

III wherein each of $R^1$, $J$, $R_H$, x, y, z, and $R^3$ is as defined above and as described in classes and subclasses herein, both singly and in combination;

and m is 2-400.

As defined generally above, m is 2-400. In certain embodiments, m is 2-10. In other embodiments, m is 2. In certain embodiments, m is about 225. In some embodiments, m is about 275. In other embodiments, m is about 110. In other embodiments, m is 40 to 60. In other embodiments, m is 60 to 90. In still other embodiments, m is 90 to 150. In other embodiments, m is 150 to 200. In some embodiments, m is 200 to 300. In still other embodiments, m is 250 to 280. In other embodiments, m is about 300 to about 375. In certain embodiments, m is selected from 50±10. In other embodiments, m is selected from 80±10, 115±10, 180±10, 225±10, or 275±10.

B. Drug Loaded Polymer Micelles

In certain embodiments, the present invention provides a micelle, having a drug encapsulated therein, comprising a multiblock copolymer of formula I:

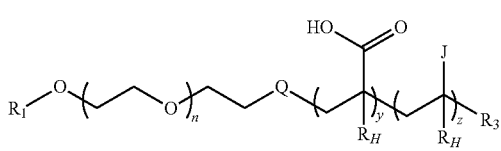

I wherein each of $R^1$, $J$, $R_H$, n, y, z, and $R^3$ is as defined above and as described in classes and subclasses herein, both singly and in combination.

In certain embodiments, the present invention provides a micelle, having a drug encapsulated therein, comprising a multiblock copolymer of formula II:

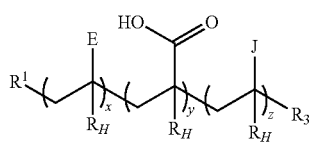

II wherein each of $R^1$, $J$, $R_H$, E, x, y, z, and $R^3$ is as defined above and as described in classes and subclasses herein, both singly and in combination.

In certain embodiments, the present invention provides a micelle, having a drug encapsulated therein, comprising a multiblock copolymer of formula III:

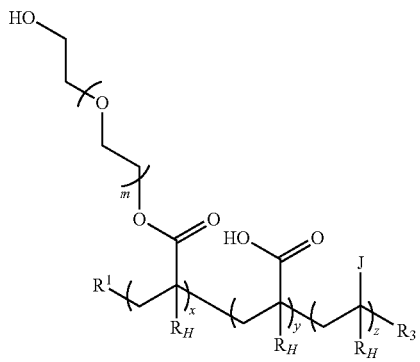

wherein each of $R^1$, J, $R_H$, m, x, y, z, and $R^3$ is as defined above and as described in classes and subclasses herein, both singly and in combination.

Hydrophobic small molecule drugs suitable for loading into micelles of the present invention are well known in the art. In certain embodiments, the present invention provides a drug-loaded micelle as described herein, wherein the drug is a hydrophobic drug selected from analgesics, anti-inflammatory agents, antihelminthics, anti-arrhythmic agents, antibacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opiod analgesics, protease inhibitors, sex hormones, stimulants, muscle relaxants, anti-osteoporosis agents, anti-obesity agents, cognition enhancers, anti-urinary incontinence agents, anti-benign prostate hypertrophy agents, essential fatty acids, non-essential fatty acids, and mixtures thereof.

In other embodiments, the hydrophobic drug is selected from one or more analgesics, anti-bacterial agents, anti-viral agents, anti-inflammatory agents, anti-depressants, anti-diabetics, anti-epileptics, anti-hypertensive agents, anti-migraine agents, immunosuppressants, anxiolytic agents, sedatives, hypnotics, neuroleptics, β-blockers, gastro-intestinal agents, lipid regulating agents, anti-anginal agents, Cox-2 inhibitors, leukotriene inhibitors, macrolides, muscle relaxants, opioid analgesics, protease inhibitors, sex hormones, cognition enhancers, anti-urinary incontinence agents, and mixtures thereof.

According to one aspect, the present invention provides a micelle, as described herein, loaded with a hydrophobic drug selected from any one or more of a Exemestance (aromasin), Camptosar (irinotecan), Ellence (epirubicin), Femara (Letrozole), Gleevac (imatinib mesylate), Lentaron (formestane), Cytadren/Orimeten (aminoglutethimide), Temodar, Proscar (finasteride), Viadur (leuprolide), Nexavar (Sorafenib), Kytril (Granisetron), Taxotere (Docetaxel), Taxol (paclitaxel), Kytril (Granisetron), Vesanoid (tretinoin) (retin A), XELODA (Capecitabine), Arimidex (Anastrozole), Casodex/Cosudex (Bicalutamide), Faslodex (Fulvestrant), Iressa (Gefitinib), Nolvadex, Istubal, Valodex (tamoxifen citrate), Tomudex (Raltitrexed), Zoladex (goserelin acetate), Leustatin (Cladribine), Velcade (bortezomib), Mylotarg (gemtuzumab ozogamicin), Alimta (pemetrexed), Gemzar (gemcitabine hydrochloride), Rituxan (rituximab), Revlimid (lenalidomide), Thalomid (thalidomide), Alkeran (melphalan), SN-38, berberine, berberrubine, epothilone A, epothilone B, epothilone C, epothilone D, ixabepilone, daunorubicin, aminopterin, cabazitaxel, and derivatives thereof.

C. Crosslinked, Drug Loaded Polymer Micelles

In addition to advances in polymer micelle technology, significant efforts have been made in the development of stimuli-responsive polymeric materials that can respond to environmental pH changes. See Chatterjee, J.; Haik, Y.; Chen, C. J. *J. App. Polym. Sci.* 2004, 91, 3337-3341; Du, J. Z.; Armes, S. P. *J. Am. Chem. Soc.* 2005, 127, 12800-12801; and Twaites, B. R.; de las Heras Alarcon, C.; Cunliffe, D.; Lavigne, M.; Pennadam, S.; Smith, J. R.; Gorecki, D. C.; Alexander, C. *J. Control. Release* 2004, 97, 551-566. This is of importance for sensitive protein and nucleic acid-based drugs where escape from acidic intracellular compartments (i.e. endosome and lysosome) and cytoplasmic release are required to achieve therapeutic value. See Murthy, N.; Campbell, J.; Fausto, N.; Hoffman, A. S.; Stayton, P. S. *J. Control. Release* 2003, 89, 365-374; El-Sayed, M. E. H.; Hoffman, A. S.; Stayton, P. S. *J. Control. Release* 2005, 104, 417-427; and Liu, Y.; Wenning, L.; Lynch, M.; Reineke, T. *J. Am. Chem. Soc.* 2004, 126, 7422-7423. Acid-sensitive delivery systems that can successfully escape the endosome and transport small-molecule chemotherapeutic drugs into the cytoplasm are also of interest since these carriers can bypass many of the cellular mechanisms responsible for multi-drug resistance. In some of these cases, the polymers are designed to respond to the significant pH gradient between the blood (pH 7.4) and the late-early endosome (pH 5.0-6.0).

In contrast to shell-crosslinked micelles, the crosslinking of multiblock copolymer micelles in accordance with the present invention is accomplished without large dilution volumes because micelle-micelle coupling does not occur. Such crosslinking will enhance post-administration circulation time leading to more efficient passive drug targeting by the EPR effect and improved active targeting using cancer-specific targeting groups. In addition, stimuli-responsive crosslinking may offer another targeting mechanism to isolate the release of the chemotherapy drug exclusively within the tumor tissue and cancer cell cytoplasm.

Crosslinking reactions designed for drug delivery preferably meet a certain set of requirements to be deemed safe and useful for in vivo applications. For example, in other embodiments, the crosslinking reaction would utilize non-cytotoxic reagents, would be insensitive to water, would not alter the drug to be delivered, and in the case of cancer therapy, would be reversible at pH levels commonly encountered in tumor tissue (pH~6.8) or acidic organelles in cancer cells (pH~5.0-6.0).

In certain embodiments, the present invention provides a drug loaded micelle comprising a triblock copolymer, wherein said micelle has a drug-loaded inner core, a crosslinked outer core, and a hydrophilic shell, wherein the multiblock copolymer is of formula IV:

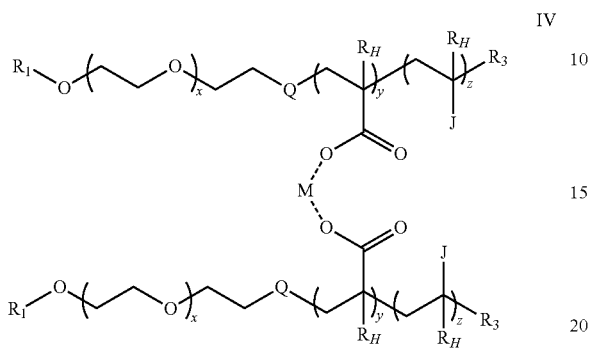

IV wherein each of $R^1$, J, $R_H$, n, y, z, and $R^3$ is as defined above and as described in classes and subclasses herein, both singly and in combination;

M is a suitable metal ion.

In certain embodiments, M is iron. In other embodiments, M is zinc. In another embodiment, M is nickel, cobalt, copper, or platinum. In other embodiments, M is calcium or aluminum. In yet other embodiments, M is strontium, manganese, platinum, palladium, silver, gold, cadmium, chromium, indium, or lead.

In certain embodiments, the present invention provides a drug loaded micelle comprising a triblock copolymer, wherein said micelle has a drug-loaded inner core, a crosslinked outer core, and a hydrophilic shell, wherein the multiblock copolymer is of formula V:

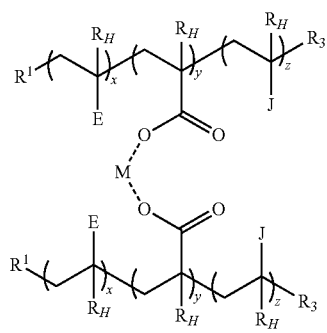

V

Wherein each of $R^1$, J, $R_H$, E, M, x, y, z, and $R^3$ is as defined above and as described in classes and subclasses herein, both singly and in combination.

In certain embodiments, the present invention provides a drug loaded micelle comprising a triblock copolymer, wherein said micelle has a drug-loaded inner core, a crosslinked outer core, and a hydrophilic shell, wherein the multiblock copolymer is of formula VI:

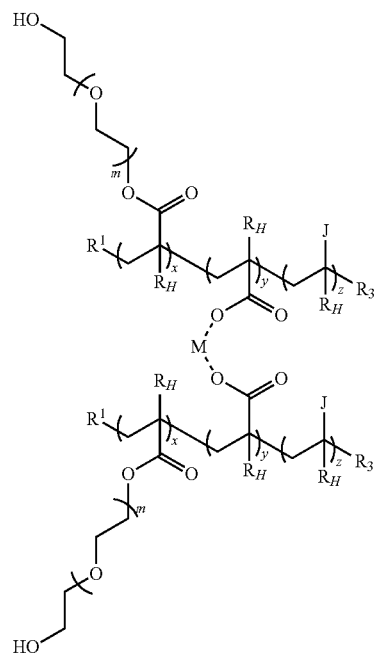

VI wherein each of $R^1$, J, $R_H$, m, M, x, y, z, and $R^3$ is as defined above and as described in classes and subclasses herein, both singly and in combination.

In certain embodiments, the crosslinking utilizes zinc-mediated coupling of carboxylic acids, a highly selective and pH-sensitive reaction that is performed in water. This reaction, which is widely used in cough lozenge applications, involves the association of zinc ions with carboxylic acids at basic pH. See Bakar, N. K. A.; Taylor, D. M.; Williams, D. R. *Chem. Spec. Bioavail.* 1999, 11, 95-101; and Eby, G. A. *J. Antimicrob. Chemo.* 1997, 40, 483-493. These zinc-carboxylate bonds readily dissociate in the presence of acid.

Scheme 1

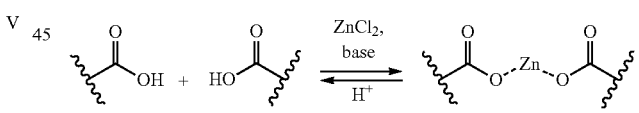

Scheme 1 above illustrates the reaction of an aqueous zinc ion (e.g. from zinc chloride) with two equivalents of an appropriate carboxylic acid to form the zinc dicarboxylate. This reaction occurs rapidly and irreversibly in a slightly basic pH environment but upon acidification, is reversible within a tunable range of pH 4.0-6.8 to reform $ZnX_2$, where X is the conjugate base. One of ordinary skill in the art will recognize that a variety of natural and unnatural amino acid side-chains have a carboxylic acid moiety that can be crosslinked by zinc or another suitable metal.

The choice of zinc as a crosslinking metal is advantageous for effective micelle crosslinking. Zinc chloride and the zinc lactate by-product are generally recognized as non-toxic, and other safety concerns are not anticipated. Pharmaceutical grade zinc chloride is commonly used in mouthwash and as a chlorophyll stabilizer in vegetables while zinc lactate is used as an additive in toothpaste and drug preparation. The reaction is reversible within a tunable pH range, selective toward carboxylic acids, and should not alter the encapsulated chemotherapy agents. While zinc has been chosen as an exemplary metal for micelle crosslinking, it should be noted that many other metals undergo acid sensitive coupling with carboxylic acids. These metals include calcium, iron and aluminum, to name but a few. One or more of these metals can be substituted for zinc.

The ultimate goal of metal-mediated crosslinking is to ensure micelle stability when diluted in the blood (pH 7.4) followed by rapid dissolution and drug release in response to a finite pH change such as those found in cancer cells. Previous reports suggest a widely variable and tunable dissociation pH for zinc-acid bonds (from approximately 2.0 to 7.0) depending on the carboxylic acid used and number of bonds formed. See Cannan, R. K.; Kibrick, A. *J. Am. Chem. Soc.* 1938, 60, 2314-2320. Without wishing to be bound by theory, it is believed that the concentration of zinc chloride and the number of aspartic acid, or other carboxylic acid-containing amino acid, repeat units in the crosslinking block will ultimately control the pH at which complete micelle disassembly occurs. The synthetic versatility of the block copolymer design is advantageous since one or more variables are tuned to achieve the desired pH reversibility. By simple adjustment of zinc chloride/polymer stoichiometry, pH-reversible crosslinking is finely tuned across the pH range of interest. For example, higher zinc concentrations yield more zinc crosslinks which require higher acid concentrations (i.e. lower pH) to dissociate. Adjustments in zinc/polymer stoichiometry will yield the desired pH reversibility, however other variables such as increasing the poly(aspartic acid) block length (i.e. 15-25 repeat units) further tune the reversible crosslinking reaction if necessary.

In another embodiment, the -M- moiety is iron. In certain embodiments, the crosslinking utilizes iron-mediated coupling of carboxylic acids. The interaction between iron and carboxylic acids in biological systems is well known in the art. See Silver, "Chemistry of Iron" 1993. Without wishing to be bound to any particular theory, it is believed that the carboxylic acid will function as a ligand in the carboxylate form (i.e. high pH) but will readily disassociate when the proton ion concentration is sufficiently high (i.e. low pH). (Scheme 2) In some embodiments, the iron moiety is $Fe^{2+}$. In some embodiments, the iron moiety is $Fe^{3+}$.

Scheme 2

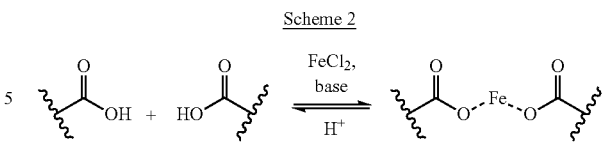

In one embodiment, drug-loaded micelles possessing carboxylic acid functionality in the outer core are crosslinked by addition of iron (II) chloride to the micelle solution. In another embodiment, drug-loaded micelles possessing carboxylic acid functionality in the outer core are crosslinked by addition of iron (III) chloride to the micelle. In certain embodiments, drug-loaded micelles possessing carboxylic acid functionality in the outer core are crosslinked by dissolving the micelles in TRIS buffer solution containing iron (II) chloride. In yet other embodiments, drug-loaded micelles possessing carboxylic acid functionality in the outer core are crosslinked by dissolving the micelles in TRIS buffer solution containing iron (III) chloride.

One skilled in the art will recognize that the M group may be either a divalent or trivalent metal ion. It is also recognized that the structures of Formula IV, V, or VI, for clarity, are represented using a divalent metal ion. In the case of a trivalent metal ion, it is understood that there may be three carboxylic acid groups bound to a single metal ion.

4. General Methods for Providing Compounds of the Present Invention

Multiblock copolymers of the present invention are prepared by methods known to one of ordinary skill in the art. Generally, such multiblock copolymers are prepared by sequentially polymerizing one or more vinyl monomers using a controlled free radical polymerization technique.

In certain embodiments, the hydrophilic polymer block is poly(ethylene glycol) (PEG) having a terminal group capable of CFRP ("PEG macroinitiator"). This PEG macroinitiator initiates the polymerization of vinyl polymers to provide the multiblock copolymers of the present invention. Preparation PEG derivatives, and methods of deprotecting the same, is described in detail in United States patent application Ser. No. 11/256,735, filed Oct. 24, 2005 and published as US 20060142506 on Jun. 29, 2006, the entirety of which is hereby incorporated herein by reference.

Scheme 3

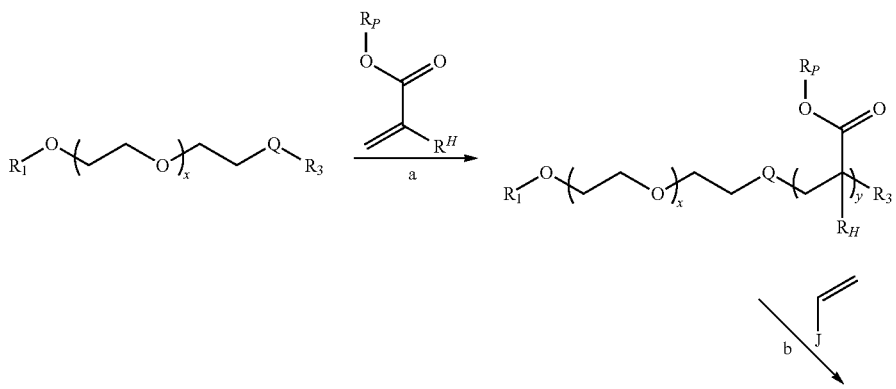

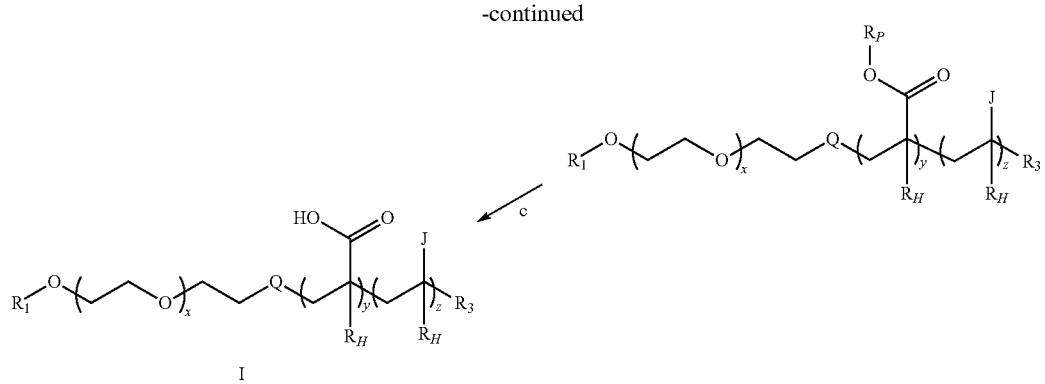

Scheme 3 above depicts the general synthesis of Formula I. A PEG chain equipped with an $R^3$ group that is capable of mediating CFRP (e.g. a nitroxide, halogen, dithioester or trithiocarbonate) is stirred with a protected acrylic acid monomer (a). Once the first monomer has been consumed, the second monomer block is introduced (b) and the polymerization run until the second monomer, or mixture of monomers, has been fully consumed. The protecting group on the carboxylic acid is then cleaved (c), affording the desired Formula I.

Scheme 4 depicts a prophetic example of how this polymerization may be performed.

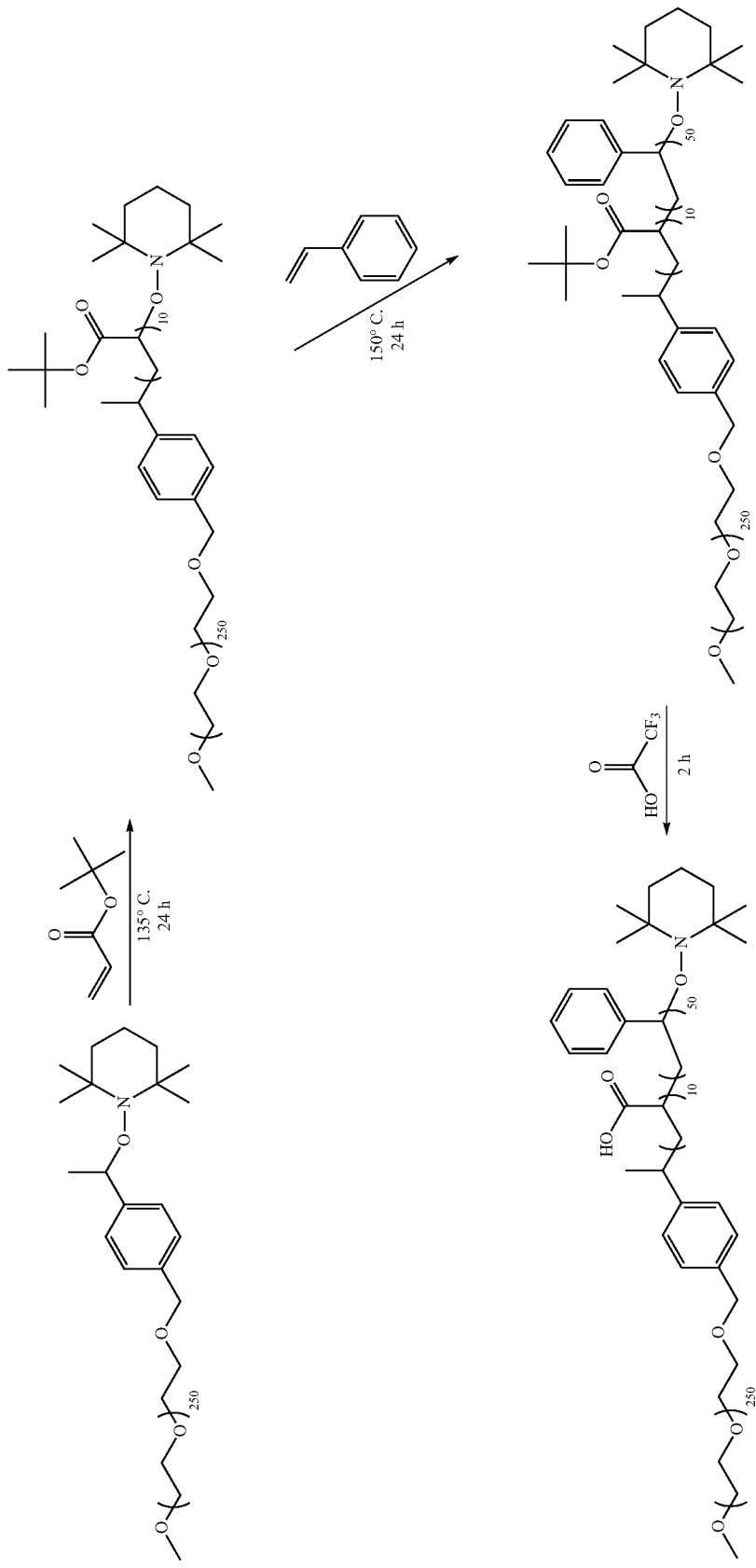

One skilled in the art will appreciate that Formula II and III can be prepared using the same methodology as presented for Formula I, simply by substituting an appropriate initiator and by polymerizing three sequential block instead of two. A prophetical example for the preparation of Formula II is shown below in Scheme 5.

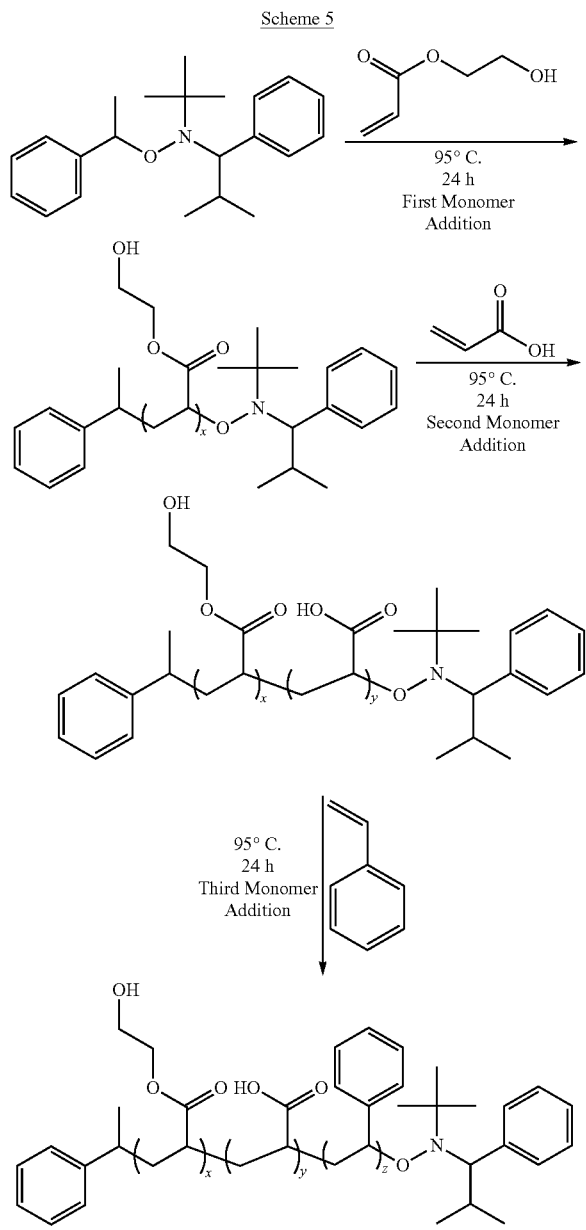

5. Uses, Methods, and Compositions

As described herein, micelles of the present invention can encapsulate a wide variety of therapeutic agents useful for treating a wide variety of diseases. In certain embodiments, the present invention provides a drug-loaded micelle, as described herein, wherein said micelle is useful for treating the disorder for which the drug is known to treat. According to one embodiment, the present invention provides a method for treating one or more disorders selected from pain, inflammation, arrhythmia, arthritis (rheumatoid or osteoarthritis), atherosclerosis, restenosis, bacterial infection, viral infection, depression, diabetes, epilepsy, fungal infection, gout, hypertension, malaria, migraine, cancer or other proliferative disorder, erectile dysfunction, a thyroid disorder, neurological disorders and hormone-related diseases, Parkinson's disease, Huntington's disease, Alzheimer's disease, a gastro-intestinal disorder, allergy, an autoimmune disorder, such as asthma or psoriasis, osteoporosis, obesity and comorbidities, a cognitive disorder, stroke, AIDS-associated dementia, amyotrophic lateral sclerosis (ALS, Lou Gehrig's disease), multiple sclerosis (MS), schizophrenia, anxiety, bipolar disorder, tauopothy, a spinal cord or peripheral nerve injury, myocardial infarction, cardiomyocyte hypertrophy, glaucoma, an attention deficit disorder (ADD or ADHD), a sleep disorder, reperfusion/ischemia, an angiogenic disorder, or urinary incontinence, comprising administering to a patient a micelle comprising a multiblock copolymer which comprises a polymeric hydrophilic block, optionally a crosslinkable or crosslinked poly(amino acid block), and a hydrophobic D,L-mixed poly(amino acid block), characterized in that said micelle has a drug-loaded inner core, optionally a crosslinkable or crosslinked outer core, and a hydrophilic shell, wherein said micelle encapsulates a therapeutic agent suitable for treating said disorder.

In other embodiments, the present invention provides a method for treating one or more disorders selected from autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease, comprising administering to a patient a multiblock copolymer which comprises a polymeric hydrophilic block, optionally a crosslinkable or crosslinked poly (amino acid block), and a hydrophobic D,L-mixed poly (amino acid block), characterized in that said micelle has a drug-loaded inner core, optionally a crosslinkable or crosslinked outer core, and a hydrophilic shell, wherein said micelle encapsulates a therapeutic agent suitable for treating said disorder.

In certain embodiments, drug-loaded micelles of the present invention are useful for treating cancer. Accordingly, another aspect of the present invention provides a method for treating cancer in a patient comprising administering to a patient a multiblock copolymer which comprises a polymeric hydrophilic block, optionally a crosslinkable or crosslinked poly(amino acid block), and a hydrophobic D,L-mixed poly (amino acid block), characterized in that said micelle has a drug-loaded inner core, optionally a crosslinkable or crosslinked outer core, and a hydrophilic shell, wherein said micelle encapsulates a chemotherapeutic agent. According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia, comprising administering a micelle in accordance with the present invention wherein said micelle encapsulates a chemotherapeutic agent suitable for treating said cancer.

Compositions

According to another embodiment, the invention provides a composition comprising a micelle of this invention or a pharmaceutically acceptable derivative thereof and a pharmaceutically acceptable carrier, adjuvant, or vehicle. In certain embodiments, the composition of this invention is formulated for administration to a patient in need of such composition. In other embodiments, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In certain embodiments, pharmaceutically acceptable compositions of the present invention are enterically coated.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the drug can be administered to a patient receiving these compositions.

It will be appreciated that dosages typically employed for the encapsulated drug are contemplated by the present invention. In certain embodiments, a patient is administered a drug-loaded micelle of the present invention wherein the dosage of the drug is equivalent to what is typically administered for that drug. In other embodiments, a patient is administered a drug-loaded micelle of the present invention wherein the dosage of the drug is lower than is typically administered for that drug.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

We claim:

1. A drug loaded micelle comprising a triblock copolymer, wherein said micelle has a drug-loaded inner core, a crosslinked outer core, and a hydrophilic shell, wherein the triblock copolymer is of formula IV:

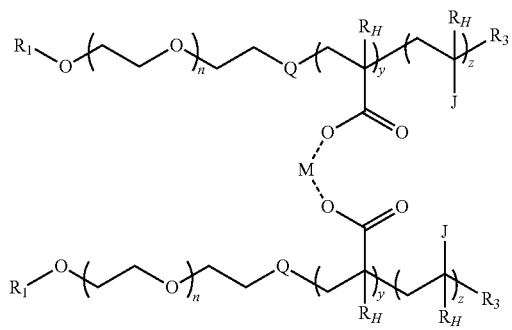

wherein:
  n is 40-500;
  y is 5-50;
  z is 10-200;
  M is iron or zinc;
  each Q group is independently selected from a valence bond or a bivalent, saturated or unsaturated, straight or branched $C_{1-20}$ alkylene chain, wherein 0-9 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
    -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
  each J group is independently selected from a saturated or unsaturated, straight or branched $C_{1-20}$ alkylene chain, wherein 0-9 methylene units of said alkylene chain are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
    -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
  $R^H$ is hydrogen, —CH$_3$, or —CH$_2$—CH$_3$;
  $R^1$ is hydrogen, —N$_3$, —CN, an amine protecting group, a protected aldehyde, a protected hydroxyl, a hydroxyl protecting group, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur;
  and $R^3$ is selected from hydrogen, a halogen, or an optionally substituted aliphatic group.

* * * * *